United States Patent
Von Berg et al.

(10) Patent No.: US 10,154,823 B2
(45) Date of Patent: Dec. 18, 2018

(54) GUIDING SYSTEM FOR POSITIONING A PATIENT FOR MEDICAL IMAGING

(71) Applicant: KONINKLIJKE PHILIPS N.V., Eindhoven (NL)

(72) Inventors: Jens Von Berg, Hamburg (DE); Jörg Sabczynski, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 15/500,378

(22) PCT Filed: May 9, 2016

(86) PCT No.: PCT/EP2016/060249
§ 371 (c)(1),
(2) Date: Jan. 30, 2017

(87) PCT Pub. No.: WO2016/184704
PCT Pub. Date: Nov. 24, 2016

(65) Prior Publication Data
US 2018/0116613 A1    May 3, 2018

(30) Foreign Application Priority Data
May 20, 2015 (EP) .................................... 15168474

(51) Int. Cl.
*A61B 6/04* (2006.01)
*A61B 6/00* (2006.01)
(Continued)

(52) U.S. Cl.
CPC .............. *A61B 6/0492* (2013.01); *A61B 6/04* (2013.01); *A61B 6/463* (2013.01); *A61B 8/40* (2013.01); *G06T 7/0012* (2013.01)

(58) Field of Classification Search
CPC ......... A61B 6/04; A61B 6/0492; A61B 6/463; A61B 8/40
See application file for complete search history.

(56) References Cited

U.S. PATENT DOCUMENTS

| | | |
|---|---|---|
| 5,539,798 A | 7/1996 | Asahina |
| 6,608,884 B1 | 8/2003 | Mazess |

(Continued)

FOREIGN PATENT DOCUMENTS

| | | |
|---|---|---|
| DE | 10008806 A1 | 12/2001 |
| JP | 2007236805 A | 9/2007 |

(Continued)

OTHER PUBLICATIONS

Talbot, J. et al "A Method for Patient Set-Up Quidance in Radiotherapy using Augmented Reality", Australasian Physical & Engineering Science in Medicine, vol. 32, No. 4, 2009.

(Continued)

*Primary Examiner* — Glen Kao
(74) *Attorney, Agent, or Firm* — Larry Liberchuk (57) ABSTRACT

The present invention relates to positioning guidance for image acquisition. In order to facilitate positioning of a patient for medical image acquisition, a guiding system (14) is provided. The system comprises a patient detecting device (22) and a patient position prescribing device (24). The patient detecting device is configured to detect an anatomy of interest (36) of a patient for image acquisition and to detect current spatial information of the anatomy of interest. The patient position prescribing device is configured to provide an initial target position (40) for the detected anatomy of interest, wherein the initial target position is provided as a reference for the image acquisition. The patient position prescribing device is further configured to register the initial target position with the current spatial information, and to determine an adapted target position (42)

(Continued)

by adapting the initial target position based inter alia on the current spatial information.

14 Claims, 4 Drawing Sheets

(51) Int. Cl.
    *A61B 8/00*     (2006.01)
    *G06T 7/00*     (2017.01)

(56) References Cited

U.S. PATENT DOCUMENTS

| | | |
|---|---|---|
| 2004/0254454 A1 | 12/2004 | Kockro |
| 2009/0088830 A1 | 4/2009 | Mohamed |
| 2010/0208037 A1* | 8/2010 | Sendai .................. A61B 6/022 348/46 |
| 2014/0104311 A1 | 4/2014 | Park |
| 2016/0213329 A1* | 7/2016 | Dirkes ................. A61B 6/4452 |

FOREIGN PATENT DOCUMENTS

| | | |
|---|---|---|
| WO | 199610949 A1 | 4/1996 |
| WO | 2013072814 A1 | 5/2013 |
| WO | 2015011987 A1 | 1/2015 |
| WO | 2015067536 A1 | 5/2015 |

OTHER PUBLICATIONS

Izadi, Shahram et al "KinectFusion: Real-Time 3D Reconstruction and Interaction using a Moving Depth Camera", UIST 11, Oct. 2011.

* cited by examiner

GUIDING SYSTEM FOR POSITIONING A PATIENT FOR MEDICAL IMAGING

CROSS-REFERENCE TO PRIOR APPLICATIONS

This application is the U.S. National Phase application under 35 U.S.C. § 371 of International Application No. PCT/EP2016/060249, filed on May 9, 2016 which claims the benefit of EP Patent Application No. 15168474.3, filed on May 20, 2015. These applications are hereby incorporated by reference herein.

FIELD OF THE INVENTION

The present invention relates to a guiding system for positioning a patient for medical image acquisition, a medical imaging arrangement, a method for guiding in positioning an anatomy of interest of a patient, a computer program element, and a computer readable medium.

BACKGROUND OF THE INVENTION

In medical imaging, for example, in X-ray imaging or in ultrasound imaging, proper positioning of a patient before a medical examination is important for the diagnostic quality of the radiograph, which therefore may require exhaustive education and training. Positioning error is one of the main reasons that cause the examinations to be repeated, which may cause not only extra costs but also additional e.g. X-ray exposure for the patient. For example, WO 2013/072814 A1 describes the positioning of an X-ray source relative to a patient.

SUMMARY OF THE INVENTION

There may be a need to provide an improved way for facilitating positioning of a patient for medical image acquisition.

The object of the present invention is solved by the subject-matter of the independent claims, wherein further embodiments are incorporated in the dependent claims. It should be noted that the following described aspects of the invention apply also for the guiding system for positioning a patient for medical image acquisition, for the medical imaging system, for the method for guiding in positioning an anatomy of interest of a patient, for the computer program element, and for the computer readable medium.

According to a first aspect of the present invention, a guiding system for positioning a patient for medical image acquisition is provided. The guiding system comprises a patient position detecting device and a patient position prescribing device. The patient detecting device is configured to detect an anatomy of interest of a patient for the medical image acquisition, and to detect current spatial information of said anatomy of interest. The patient position prescribing device is configured to provide an initial target position for the detected anatomy of interest during the image acquisition, and to register a subset of the initial target position with the current spatial information of the anatomy of interest insofar said subset is clinically irrelevant for the medical image acquisition thereby providing for an adapted target position. Advantageously, insofar the medical image acquisition feasibly allows, i.e. without compromising clinical qualities, the initial target position (e.g. a virtual scene of a virtual patient in the correct position) is adapted (or registered) to the current spatial information (e.g. position, pose and size) of the anatomy of interest. In other words, aspects of the initial target position that are irrelevant for a successful medical image acquisition are being registered with (i.e. adapted to) the patient and more specifically the current spatial information of the anatomy of interest, whereas aspects that are relevant for a successful medical image acquisition are being preserved (i.e. remain unchanged). The result of such partially registering is the adapted target position. Herein, the aspects relevant for a successful medical image acquisition may be derived from generally available sources such "Positioning in Radiography" by Swallow, Naylor, Roebuck and Whitley, Butterworth Heinemann, Oxford, $11^{th}$ edition, 1986. Hence, the guiding system according to the present invention enables a patient and a radiographer to focus on positioning the relevant aspects of the pose for image acquisition, for example, adjusting forearm and fingers for a lateral thumb image acquisition, without the need of adjusting the irrelevant aspects of the pose, such as translating the arm or re-positioning the shoulder in case of a lateral thumb image acquisition. This may save preparation time e.g. for an X-ray image examination and also mean increased comfort for patients and staffs. Moreover, the adaption of the initial target position to the size of the anatomy of interest allows a better match of the shape of the anatomy of interest, which may make it easier and more precise for the alignment of the patient with the adapted target position.

The initial target position may be based on best practice patient pose models, for example as discussed in aforementioned source.

The term "patient detecting device" relates to a device capable of analyzing a real-world object (e.g. a patient or an anatomy of interest of a patient) or environment (e.g. a treatment room) to collect data on its shape (e.g. a patient's external contour) and possibly its appearance (e.g. color). For certain applications, the patient detecting device may be a camera, such as a 3D scanner, for determining the patient's external contour and also depth information. For other applications, the inner anatomy of a patient (e.g. bones) may be determined in a pre-shot imaging phase of X-ray image acquisition. In this case, the X-ray image acquisition device (including an X-ray source and an X-ray detector) may be referred to as patient detecting device.

The term "current spatial information" may also be referred to as current spatial arrangement or current spatial position.

The term "initial target position" may also be referred to as initial target arrangement; and the term "adapted target position" may also be referred to as modeled or adapted target arrangement or modeled target position.

The terms "clinically irrelevant subset of the initial target position" or "clinically irrelevant subset" relate to a subset of the initial target position being irrelevant for a successful medical image acquisition. In other words, adjusting such clinically irrelevant subset of the initial target position will not affect (or at least minimally affect) clinical qualities of the medical image examination. It is noted that the clinically irrelevant subset may largely be determined by the examination type at hand. For example, the shoulder (and hence its spatial position, pose and/or size) position may be considered a clinically irrelevant subset of the initial target for a lateral thumb medical image acquisition.

In the following, "clinically irrelevant aspects of the initial target position" are simply referred to as "irrelevant aspects". Likewise, "clinically relevant aspects of the initial target position" are simply referred to as "relevant aspects".

In an example of the guiding system according to the present invention, the patient position prescribing device is configured to generate image data of the adapted target position; and comprising a display device configured to display the generated image data of the adapted target position in an overlaid manner with the anatomy of interest. In this manner, visual guidance information is displayed to a user (e.g. a radiographer) for the purpose of aligning the anatomy of interest with the adapted target position.

In another example of the guiding system according to the present invention, the adapted target position comprises augmented reality information, wherein said augmented reality information comprises a 3D virtual model of the detected anatomy of interest. Advantageously, the 3D virtual model may provide an intuitive guidance to the radiographer for proper positioning of the anatomy of interest relative to the adapted target position. The term "augmented reality information" relates to computer-generated information, such as sound, video, graphics, etc., which is supplemented to a live direct or indirect view of a real-world environment (e.g. an anatomy of interest). For example, for guiding the positioning of a patient, the augmented reality information may comprise a 3D virtual model representing the adapted target position and may hint on a deviation between the current spatial information of the anatomy of interest and the adapted target position, which information may be displayed e.g. as "10° off target, 20 cm off target". There are several methods to create the 3D virtual model. In an example, a 3D virtual model is realized by a computer-animated film. In a further example, a correctly positioned anatomy of interest is analyzed and its shape data are collected for modeling by a 3D surface scanner. As the anatomy may also relate to an inner anatomy, a 3D virtual model may include a model of an inner anatomy of a patient, e.g. bones.

In another example of the guiding system according to the present invention, the current spatial information comprises a current position, a current pose and/or a current size. Advantageously, this allows the positioning information to better represent patients with different shapes, such as tall or small patients, bold or slim patients. Furthermore, the alignment of the patient with the adapted target position may be easier and more accurately achievable when the adapted target position and the anatomy match in respect of position, pose as well as size.

In another example of the guiding system according to the present invention, the display device is configured to display the adapted target position partly opaque. This has the effect that the relative position in depth between the adapted target position and the anatomy of interest is perceptible.

The image data adapted target position may be adjusted to be partially opaque, which allows the visualization of the (depth-related) discrepancies between the adapted target position and the anatomy of interest. This rendering may thus allow a more precise visual guidance for positioning than transparent augmented reality.

In another example of the guiding system according to the present invention, the display device is a head-wearable display, through which a user can view the anatomy of interest, wherein the adapted target position is provided in an overlaid manner with the anatomy of interest viewed through the head-wearable display.

Advantageously, no eye-to-display calibration is needed, which allows a user directly (visually) enter into the augmented environment, providing direct 3D interaction. Further, as a camera or a computing device may be integrated into the head-wearable display, no additional equipment is required, for example, within a treatment room.

A head-wearable display, also referred to as optical see-through display, or head-mounted display (HMD), may be a semi-transparent display (monocular HMD) or two semi-transparent displays for both eyes (binocular HMD). Examples are products like Epson Moverio BT 200, Google glass, Vuzix, or Meta spac glasses.

In another example of the guiding system according to the present invention, the display device is a monitor, wherein the patient detecting device is configured to provide a visual representation of the anatomy of interest, and wherein he adapted target position is provided in an overlaid manner with said visual representation.

The monitor may offer the advantage of being visible to any person in the room, also the patient. Hence, the patient can adjust the pose according to the augmented reality guidance on the screen of the monitor, thus reducing the preparation time e.g. prior to an X-ray image acquisition. The monitor may also be provided to show another perspective of the anatomy of interest in addition to a head-wearable display.

According to a second aspect of the present invention, a medical imaging arrangement is provided. The medical imaging arrangement comprising a guiding system according to one of the examples described above. The medical imaging arrangement furthermore comprises an image acquisition system comprising a medical imaging source and a medical imaging detector. Herein, the medical imaging source is configured to provide an imaging field detected by the medical imaging detector.

Advantageously, an operator is guided visually how to precisely position a patient. This may be used to support less trained operators for proper positioning of a patient before an X-ray image acquisition, as well as teaching and education for other modalities like ultrasound, MRI (Magnetic resonance imaging), CT (computed tomography), and others. Further, this may provide a better assistance of the medical imaging system in patient positioning and the planning of radiation exposure for an X-ray examination.

In an example of the medical imaging arrangement according to the present invention, the medical imaging arrangement comprises at least one of the group of an X-ray imaging arrangement and an ultrasound imaging arrangement. Herein, the X-ray imaging system may be selected from the group of: CT scanner, C-arm scanner, mammography scanner, tomosynthesis scanner, diagnostic X-ray scanner, and pre-clinical imaging scanner. For X-ray imaging, the medical imaging source and detector refer to an X-ray source and an X-ray detector, respectively. For ultrasound imaging, the medical imaging source and detector may refer to an ultrasonic transducer, which both transmits and receives ultrasonic signals. The term "imaging field" relates to, for example, X-ray radiation field in X-ray imaging, ultrasound field in ultrasound imaging, magnetic field in MRI, etc.

In an example of the medical imaging arrangement according to the present invention, the medical imaging arrangement is further configured to provide and display a graphical target source representation comprising augmented reality information indicating a target position of the medical imaging source for the image acquisition, and/or a graphical target detector representation comprising augmented reality information indicating a target position of the medical imaging detector for the image acquisition. Advantageously, the augmented reality information may provide hints to align the medical imaging source and the medical imaging detector. For example, this may include the hints on the deviation of the current spatial information of the X-ray source from the target position may be displayed as "10° off target, 20 cm off target". This information may also be provided as sound, for example, voice command.

According to a third aspect of the present invention, a method is provided for guiding the positioning of an anatomy of interest of a patient. The method comprises the following steps:

a) detecting an anatomy of interest of a patient for image acquisition;
b) detecting current spatial information of the detected anatomy of interest;
c) providing an initial target position for the detected anatomy of interest during the medical image acquisition;
d) registering a subset of the initial target position with the current spatial information of the anatomy of interest insofar said subset is clinically irrelevant for the medical image acquisition;
e) determining an adapted target position based on said registration.

In an example of the method according to the present invention, the method further comprises the following steps:

f) generating image data of the adapted target position; and
g) displaying the generated image data of the adapted target position in an overlaid manner with the anatomy of interest as graphical positioning information for alignment of the anatomy of interest for the image acquisition.

According to an example, the method further comprises:

h) providing and displaying a graphical target source representation comprising augmented reality information indicating a target position of the medical imaging source for the image acquisition, and/or a graphical target detector representation comprising augmented reality information indicating a target position of the medical imaging detector for the image acquisition.

According to a fourth aspect of the present invention, a computer program element for controlling an apparatus is provided, which, when executed by a processing unit, is adapted to perform the method steps.

According to a fifth aspect of the present invention, a computer readable medium having stored the program element discussed previously is provided.

According to an aspect of the present invention, an augmented reality system is proposed to support the positioning of a patient, e.g. for an X-ray acquisition. Best practice patient pose models are registered with the current spatial information, such as position, pose and size, of the patient to provide an adapted position to visually guide an operator how to precisely position the patient. For example, by depth sensing the patient, a pose model may be adapted in pose, position, and/or size to the patient, insofar as it concerns clinically irrelevant subsets and/or aspects of the pose model. Further, partly opaque (semi-transparent) overlay or superimposition of adapted best practice patient pose models with the patient allows for better depth perception. The augmented reality system may also be configured to support the positioning e.g. of an X-ray source and/or an X-ray detector for an X-ray acquisition. This can be used to assist a radiographer in diagnostic X-ray to position the patient correctly. If no radiographer is available (e.g. in some rural areas), the augmented reality system can help untrained personal to position the patient correctly. It is also applicable in the training of radiographers or other personal to position patients, as well as in the education for other modalities like ultrasound, MRI, CT, etc.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
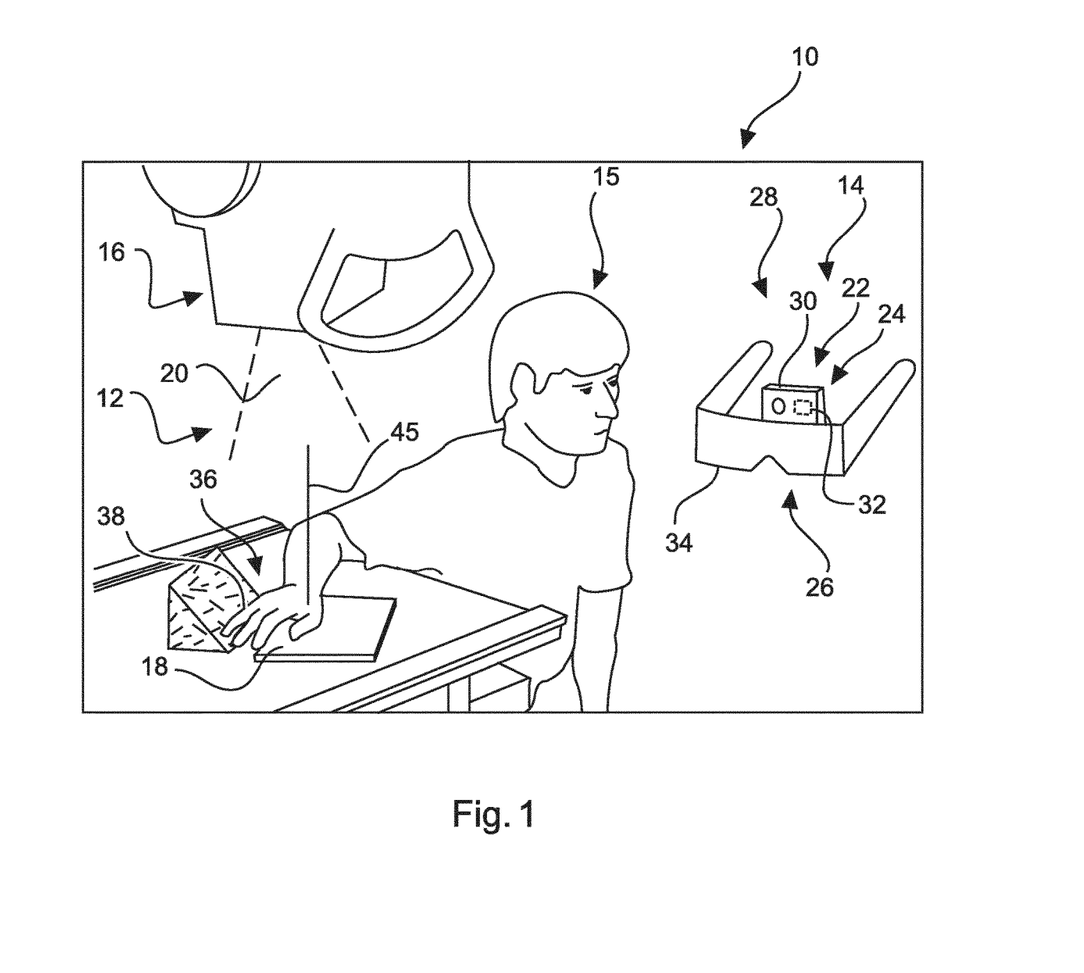
FIG. 1 shows an example of a medical imaging arrangement in a schematic view.

FIG. 1 shows an example of a medical imaging arrangement 10, for example an X-ray imaging arrangement as shown in FIG. 1, or an ultrasound imaging arrangement (not further shown).

It should also be noted that although the following discussion is related to an X-ray imaging system, i.e. an example of the medical imaging arrangement 10, the principle is also applicable to other imaging modalities, for example, ultrasound, MRI, CT, etc. However, for simplicity, the guiding in other medical imaging modalities is not further discussed.

The medical imaging arrangement 10 comprises an image acquisition system 12 (e.g. an X-ray acquisition system shown in FIG. 1) and a guiding system 14 for positioning a patient 15 for medical image acquisition, e.g. for X-ray or ultrasound image acquisition.

The medical acquisition system 12 comprises a medical imaging source 16 (e.g. an X-ray source as shown in FIG. 1) and a medical imaging detector 18 (e.g. an X-ray detector as shown in FIG. 1). The medical imaging source 16 is configured to provide an imaging field 20 (e.g. an X-ray radiation field as shown in FIG. 1) detected by the medical imaging detector 18.

The guiding system 14 comprises a patient detecting device 22 and a patient position determination device 24.

The patient detecting device 22 may be capable of detecting a patient's external contour. For example, the patient detecting device 22 may be a depth camera, an infrared camera, an ultrasound sensor, etc. The patient detecting device 22 may also be capable of detecting an inner anatomy of interest, such as bones or a target organ. For example, the patient detecting device 22 may be an X-ray image acquisition device, which acquires the image of the inner anatomy of interest by generating an X-ray pre-shot.

The position determination device 24 may relate to a computing device, for example, a built-in computing unit, a processor, or a desktop computer.

An optional display device 26 may be provided, which may relate to any suitable displays for visualization of the information. Examples include monitors, hand held devices and HMD (head-mounted display).

The patient detecting device 22, the patient position determination device 24, and the display device 26 may be connected via any suitable ways including wireless communication (e.g. Bluetooth or WLAN (wireless local area network)) or wired communication (e.g. via cables).

For example, the guiding system 14 in FIG. 1 is provided as a head-wearable guiding system 28, which, for example, brings an integrated camera 30 as an example of the patient detecting device 22, a built-in computing device 32 (not shown in detail) as an example of the patient position prescribing device 24, and a head-wearable display 34 as an example of the display device 26.

In a further example (not further shown), the head-wearable guiding system 28 comprises the integrated camera 30 and the head-wearable display 34, whereas the patient position prescribing device 20 is provided as a high-performance desktop computer communicated with the integrated camera 30 and the head-wearable display 34 via WLAN, for example. In this manner, the head-wearable guiding system 28 may provide direct volume rendering without sacrificing the speed of frame rates due to the hardware support of the high performance desktop computer.

The patient detecting device 22 is configured to detect an anatomy of interest 36, such as a hand 38, of the patient 15 for image acquisition, and to detect current spatial information (e.g. position, pose, or size) of the anatomy of interest 36.

The patient position prescribing device 24 is configured to provide an initial target position 40 (see an example in FIG. 2A) for the detected anatomy of interest 36. The initial target position 40 is provided as a reference for the medical image acquisition. The patient position prescribing device 24 is furthermore configured to register a subset of the initial target position 40 with the current spatial information of the anatomy of interest insofar said subset is clinically irrelevant for the medical image acquisition thereby providing for an adapted target position 42 (see an example in FIG. 2B).

The initial target position 40 may also be referred to as reference position, which refers to a virtual scene of a virtual patient in the correct position, or right pose. There are several methods to create virtual patient in the right poses (i.e. to create the initial target position or reference position). In an example, a patient is modeled in 3D as it is done in computer animated films. Another example is to record a correctly positioned patient (or model) with a camera (e.g. a 3D surface camera). The initial target position 40 of an inner anatomy of interest, such as a tumor, may be realized by using the previously recorded data, e.g. from the planning CT scan.

In an example, the initial target position 40 is associated with a predetermined examination type. During positioning procedure, the predetermined examination type is selected from i) a list in a database that comprises a plurality of examination types, ii) an electronic scheduling system, and/or iii) a plurality of tokens, each token associated with a respective predetermined examination type.

In other words, a user (e.g. a radiographer) may record scenes as initial target positions and add them to the database, when the patient is correctly positioned. The database may comprise a variety of anatomical structures of a patient including external anatomies (e.g. legs or hands) or inner anatomies (e.g. bones). The database may further comprise a set of virtual patients with different sex, weight, height, age, etc. Repeating the modeling or recording for each foreseen imaging situation may fill a database of virtual scenes.

During positioning procedure, a user (e.g. a radiographer) may select the planned examination type from a list, such as "ankle, subtalar joint, right, oblique-lateral". The examination type may also come automatically from a scheduler or an electronic scheduling system that integrates the radiology workflow. The virtual scene with the virtual patient may be retrieved from the database and displayed e.g. in the head-wearable display. Alternatively, there may be different tokens (markers) for different examination types. To each token a different virtual scene is attached, which corresponds to the examination type. This means, instead interacting with a computer (e.g. selecting the planned examination type from a list), a radiographer may use physical objects, e.g. the tokens, to select the desired examination type.

The adapted target position 42 may be referred to as modeled target position. Since it may be the position actually observed by an observer during the alignment, the adapted target position 42 may also be referred to as observed position. Hence, the patient position prescribing device 24 is configured to bring the target position from the reference position (i.e. the initial target position 40) to the observed position (i.e. adapted target position 42), and the observed position better matches the current spatial information.

The registration may be performed by analyzing the anatomy of interest 36 and estimating the positions of certain landmarks, e.g. body joints. These landmarks can be registered with the corresponding landmarks in the graphical target anatomy representation.

Alternatively, the registration may be carried out by attaching tokens or markers on certain positions of the anatomy of interest or the patient. These tokens or markers may be tracked, e.g. by a camera. When the token or marker is moved (i.e. the pose of the anatomy is changed), the virtual patient adapts to the movement of the token or marker as well.

Optionally, the patient position prescribing device 24 is further configured to generate image data of the adapted target position 42.

The optional display device 26 is configured to display image data of the adapted target position 42 in an overlaid manner with the anatomy of interest 36 as graphical positioning information for alignment of the anatomy of interest 36 for the image acquisition.

The image data of the adapted target position 40 may be visualized in several ways. In an example, the adapted target position (e.g. a 3D virtual model) is displayed with an opaque wireframe (or contour or outline) around it. In a further example, the adapted target position is an opaque surface model.

In an example, the display device 26 is a head-wearable display 34 (as shown in FIG. 1), through which a user can view the anatomy of interest 36. The adapted target position 42 is provided as an overlaid manner with the anatomy of interest 36 viewed through the head-wearable display 34.

This has the advantage that the person preparing the patient for the acquisition is using his/her natural visual field.

In a further example (not shown), the display device 26 is a monitor. The patient detecting device 22 is configured to provide a visual representation of the anatomy of interest in its current position. The adapted target position 42 is configured to be provided in an overlaid manner with the visual representation.

The monitor may also be provided to show the patient from another perspective in addition to the head-wearable display. For example, the monitor may be placed at the operating device of the X-ray machine. A patient detecting device, such as a depth camera, may be attached to the X-ray machine at a fixed position. The user may have an occasional look at the monitor to assure proper patient positioning.

The adapted target position 42 is provided for guiding in positioning the anatomy of interest 36 of the patient 15 relative to the medical imaging arrangement for image acquisition.

It is noted that the display device 26 is only provided as an option. In a further example (not shown), the guiding system 14 is not provided with a display device. For example, the adapted target position 42 is determined, which is used to control a movable anatomy support (e.g. an imaging coil for MRI) to automated re-arrange (re-align) the anatomy of interest for the image acquisition. In a further example, the adapted target position 42 is determined, and a voice command is provided for guiding in positioning the anatomy of interest, for example, "moving your forearm 2 cm to the left". In such examples, the display of the adapted target position would not be necessary.

Figure 2A:
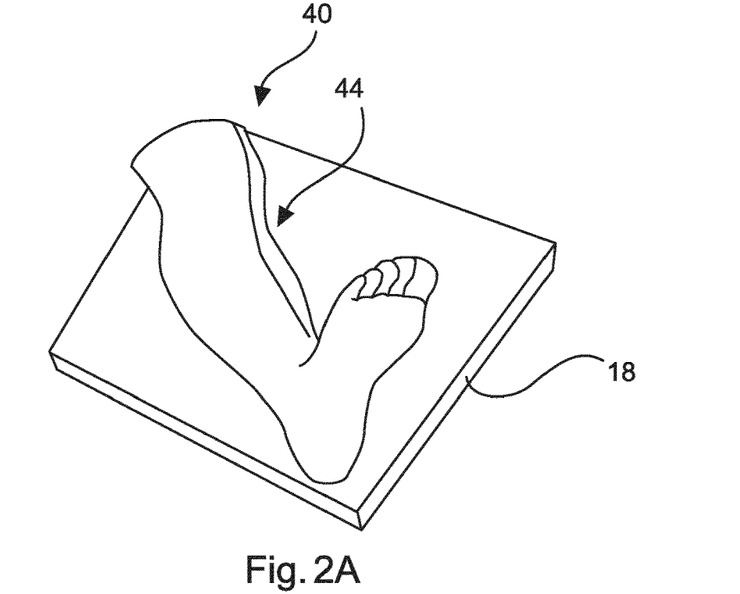
FIG. 2A shows an example of an initial target position.
Figure 2B:
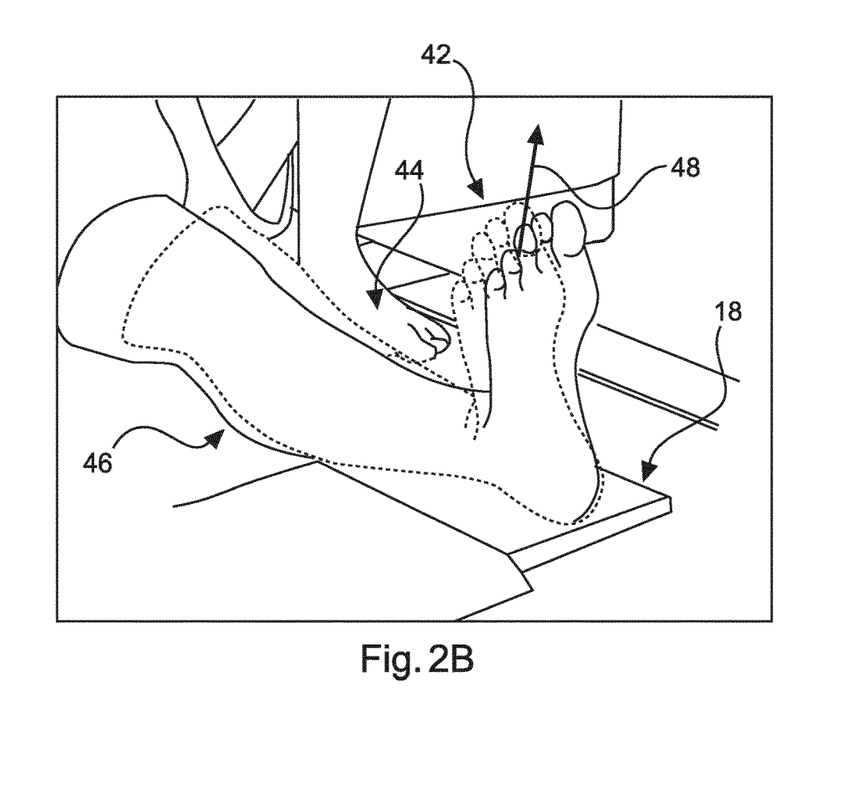
FIG. 2B shows an example of an adapted target position of FIG. 2A.

FIG. 2A shows an example of the initial target position 40 e.g. stored in a database, and FIG. 2B shows an example of the adapted target position 42, e.g. through the head-wearable display 34 (see FIG. 1).

As indicated above, the initial target position 40 is a virtual scene of a virtual patient in the correct position, or right pose. The initial target position 40 may be obtained by recording a correctly positioned patient (or model) with a camera (e.g. a 3D surface camera) and stored in a database. Hence, in the initial target position 40, the position of the virtual patient (or anatomy) may be fixed to a reference structure (e.g. an X-ray detector). Although the initial target position 40 may be used for guiding purposes, this practically leads to some complications. For example, a patient has to be positioned exactly like the virtual patient, which may be not necessarily acquired for the acquisition.

For example, the initial target position 40 in FIG. 2A is obtained by recording a correctly posed virtual limb 44 diagonally (from corner to corner) placed on the medical imaging detector 18. It is, however, not necessary to position a patient' limb 46 (see FIG. 2B) exactly like the correctly posed virtual limb 44. Some translation of the patient's limb 46 on the surface of the medical imaging detector 18 may also be acceptable for the image acquisition, as long as the patient's limb 46 is positioned within the medical imaging detector 18.

The adapted target position 42 (indicated with dotted lines) in FIG. 2B is achieved by registering the initial target position 40 in FIG. 2A, at least insofar it concerns clinically irrelevant aspects of the initial target position 40, with the current spatial information of the anatomy of interest 36, i.e. the patient's limb 46.

In an example, shown as an option in FIG. 2B, the current spatial information may comprise a current position of the anatomy of interest 36. The adapted target position 42 is adaptable to the current position of the anatomy of interest 36.

The term "position" relates to translational position (or liner position) as well as angular position (or orientation or rotation) of a virtual patient, which may include one or a plurality of anatomies. For example, the correctly posed virtual limb 44 may be rotated around an axis perpendicular to the medical imaging detector 18 (e.g. X-ray detector as shown in FIG. 2B) or translated on the surface of the medical imaging detector 18 to better match the current position of the patient's limb. The adaption to the current position may be viewed as a rigid transformation of a virtual patient.

In a further example, shown as an option in FIG. 2B, the current spatial information may comprise a current pose of the anatomy of interest 36. The adapted target position 42 is adaptable to the current pose of the anatomy of interest 36.

The term "pose" relates to the relative position between the anatomies inside a virtual patient. For example, the pose of the correctly posed virtual limb 44 may relate to the right-angle flexion at the ankle joint.

It is noted that only those aspects of the patient pose being relevant for the acquisition are preserved (i.e. unchanged), whereas irrelevant aspects are registered (i.e. adapted) with the patient.

Taking FIG. 1 for example, as the position of the forearm and fingers with respect to an optical axis 45 at the center of the medical imaging detector 18 is crucial for a successful acquisition, the forearm and fingers of a virtual patient should be locally synthesized precisely from the best practice model, i.e. the pose of the forearm and fingers in the virtual patient should remain unchanged. On the other hand, the shoulder and upper arm of the virtual patient may be registered with i.e. adjusted to the patient anatomy, since they are irrelevant for the acquisition.

In the example of FIG. 2B, this means (slight) rotation of the foot and (slight) adjustment of the angle at the ankle joint, without the need of translating and rotating the whole leg. In the example of FIG. 1, this means (slightly) adjustment of the forearm and fingers, without the need of translating and rotating the whole arm as well as the need of adjusting the shoulder or upper arm. This may reduce the effort for proper positioning a patient e.g. prior to an X-ray acquisition, especially for a less trained radiographer. As the patient only focuses on the alignment of the relevant aspects for the acquisition, the positioning errors may be reduced. Furthermore, this may also reduce the preparation time and thus increase the workflow.

In a further example, shown as an option in FIG. 2B, the current spatial information may comprise a current size of the anatomy of interest 36. The adapted target position 42 is obtained by adapting the initial target position to the current size of the anatomy of interest 36.

In other words, the adapted target position 42 may be obtained with some scaling parameters based on the size of the detected anatomy of interest 36. For example, the adapted target position of a limb may be rendered large in case of a large patient. In the example of FIG. 2B, this means that the correctly posed virtual limb 44 has (exactly) size of the patient's limb 46.

This allows the positioning information to better represent patients with different shapes, such as tall or small patients, bold or slim patients. Even for the same patient, changes to patient geometry are likely to occur as their weight changes. Therefore, when the virtual patient and the real patient agree in the size of the anatomy of interest (e.g. the patient's limb 46 in FIG. 2B), the alignment of the anatomy of interest with the virtual model may be much easier and more accurately achievable.

As a further option, the image data of the adapted target position 42 is partly opaque such that the relative position in depth between the adapted target position 42 and the anatomy of interest 36 is perceptible. This provides occlusion, which is a visual clue for an observer to estimate depth, especially the relative depth of two objects (adapted target position 42 and anatomy of interest 36) to each other, even in monoscopic view. Here, the patient pose is determined in the scene and thus the depth information is available for it. This allows scene rendering where patient surface and model surface occlude each other locally, according to their relative positions. Such rendering allows a more precise visual guidance for positioning than transparent augmented reality alone. In addition, it does not rely on stereoscopic depth perception as the only depth clue. This is an important advantage, since a portion of the population have no or impaired stereoscopic vision.

As a further option, the medical imaging arrangement 10 is further configured to provide and display a graphical target source representation 48 comprising augmented reality information indicating a target position of the medical imaging source 16 for the image acquisition, and/or a graphical target detector representation (not further shown) comprising augmented reality information indicating a target position of the medical imaging detector 18 for the image acquisition. For example, the graphical target source representation comprises an arrow 50, shown as part of the virtual scene describing the correct position of the medical imaging source 16 (see FIG. 1).

Although not illustrated, the graphical target source representation 48 may also comprise a 3D virtual model of the medical imaging source 16 (e.g. an X-ray imaging source as shown in FIGS. 1 and 2B, or an ultrasound transducer (not further shown)) describing the correct position of the medical imaging source 16. The deviation of the medical imaging source 16 from the target position may also be displayed, for example, as "20 cm off target". Likewise, the graphical target detector representation may also comprise various augmented reality information.

Figure 3:
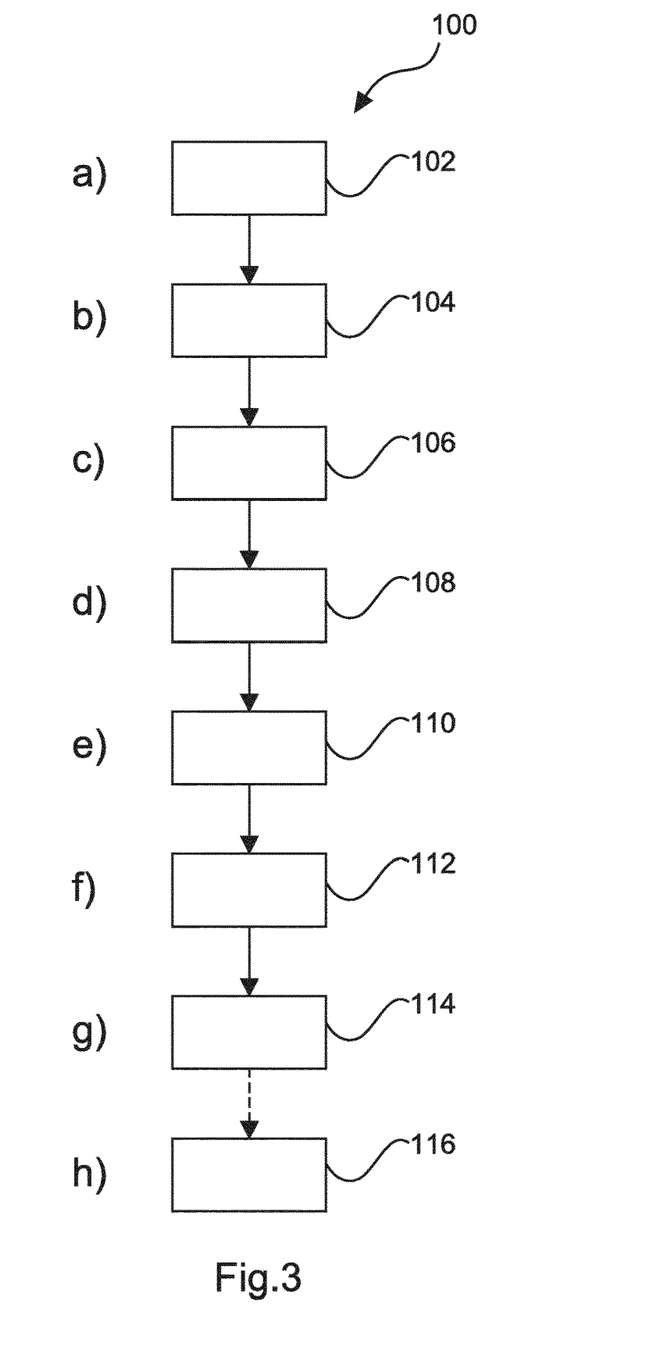
FIG. 3 shows basic steps of an example of a method for guiding in positioning an anatomy of interest of a patient.

FIG. 3 shows a method 100 for guiding in positioning an anatomy of interest of a patient. The method comprises the following steps:

In a first step 102, also referred to as step a), an anatomy of interest of a patient is detected for image acquisition.

In a second step 104, also referred to as step b), current spatial information of the detected anatomy of interest is detected.

In a third step 106, also referred to as step c), an initial target position is provided for the detected anatomy of interest.

In a fourth step 108, also referred to as step d), a subset of the initial target position is registered with the current spatial information insofar said subset is clinically irrelevant for the medical image acquisition.

In a fifth step 110, also referred to as step e), an adapted target position is determined based on said registration.

Figure 4:
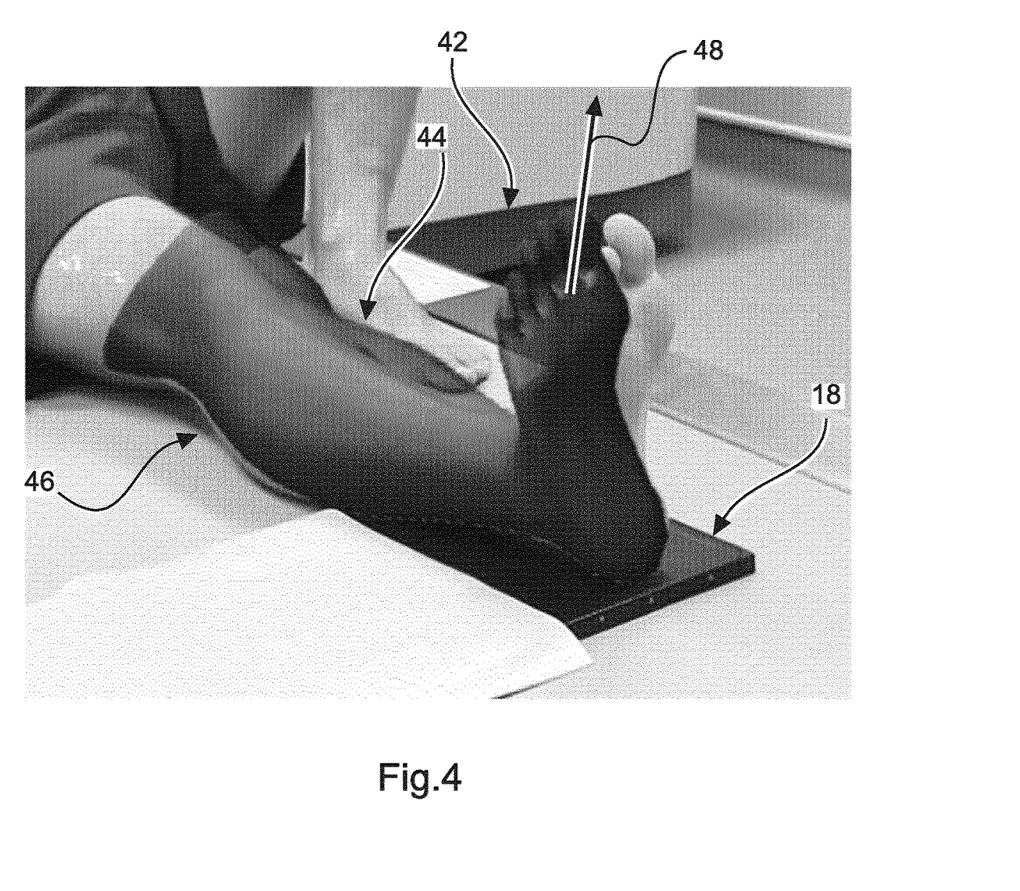
FIG. 4 shows a photographic image of the example of FIG. 2B.

In an example, shown as an option in FIG. 4, the method 100 further comprises the following steps:

In a sixth step 112, also referred to as step f), image data of the adapted target position is generated.

In a seventh step 114, also referred to as step g), the generated image data of the adapted target position is displayed in an overlaid manner as graphical position information for alignment of the anatomy of interest for the image acquisition.

Step a) may also be referred to as detecting or monitoring step.

Step b) may also be referred to as tracking step, which relates to the spatial information estimation (position estimation, pose estimation, and/or size estimation) of anatomy of interest.

Steps c) and d) together may also be referred to registration step.

Step e) may also be referred to as adaption step.

Step g) may also be referred to as visualization and data representation step.

In an example, the adapted target position comprises augmented reality information. The augmented reality information comprises a 3D virtual model of the detected anatomy of interest.

In a further example, shown as an option in FIG. 4 (indicated with a dotted line connection), the method 100 further comprises: h) providing and displaying 116 a graphical target source representation comprising augmented reality information indicating a target position of the medical imaging source for the image acquisition, and/or a graphical target detector representation (not further shown) comprising augmented reality information indicating a target position of the medical imaging detector for the image acquisition.

For a better understanding, FIG. 4 shows a photographic image according to the drawing of FIG. 2B. Hence, the same reference numbers are indicated with respect to the FIG. 2B. In order to avoid unnecessary repetition, a description with relation to FIG. 4 is thus not necessary.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid state medium supplied together with or as part of other hardware, but may also be distributed in other forms, such as via the internet or other wired or wireless telecommunication systems. However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A guiding system for positioning a patient for medical image acquisition, the system comprising:
    a patient position detecting device; and
    a patient position prescribing device;
    wherein the patient position detecting device is configured: to detect an anatomy of interest of a patient for the medical image acquisition; and to detect current spatial information of the anatomy of interest; and
    wherein the patient position prescribing device is configured: to provide an initial target position, being a virtual scene of a virtual patient in the correct position, for the detected anatomy of interest during the image acquisition and to register a subset of the initial target position with the current spatial information of the anatomy of interest insofar said subset is clinically irrelevant for the medical image acquisition thereby providing for an adapted target position.

2. Guiding system according to claim 1, wherein the patient position prescribing device is configured to generate image data of the adapted target position; and comprising a display device configured to display the generated image data of the adapted target position in an overlaid manner with the anatomy of interest.

3. Guiding system according to claim 2, wherein the adapted target position comprises augmented reality information; and wherein the augmented reality information comprises a 3D virtual model of the detected anatomy of interest.

4. Guiding system according to claim 2, wherein the display device is configured to display the adapted target position partly opaque.

5. Guiding system according to claim 4, wherein the display device comprises a head-wearable display, through which a user can view the anatomy of interest, wherein the adapted target position is provided in an overlaid manner with the anatomy of interest viewed through the head-wearable display; and/or
    a monitor, wherein the patient detecting device is configured to provide a visual representation of the anatomy of interest, and wherein the adapted target position is provided in an overlaid manner with said visual representation.

6. Guiding system according to claim 1, wherein the current spatial information comprises a current position, a current pose and/or a current size.

7. Guiding system according to claim 1, wherein the initial target position is associated with a predetermined examination type selected from:
    a list in a database that comprises a plurality of examination types;
    an electronic scheduling system; and/or
    a plurality of tokens, each token associated with a respective predetermined examination type.

8. A medical imaging arrangement, comprising:
    a guiding system according to claim 1;
    and an image acquisition system
    comprising a medical imaging source and a medical imaging detector; wherein the medical imaging source is configured to provide an imaging field detected by the medical imaging detector.

9. Medical imaging arrangement according to claim 8, wherein the medical imaging arrangement comprises at least one of the group of:
    an X-ray imaging arrangement; and
    an ultrasound imaging arrangement.

10. Medical imaging arrangement according to claim 9, wherein the medical imaging arrangement is further configured to provide and display:
    a graphical target source representation comprising augmented reality information indicating a target position of the medical imaging source for the image acquisition; and/or
    a graphical target detector representation comprising augmented reality information indicating a target position of the medical imaging detector for the image acquisition.

11. A method for guiding positioning of an anatomy of interest of a patient, comprising:
    detecting an anatomy of interest of a patient for a medical image acquisition;
    detecting current spatial information of the detected anatomy of interest;
    providing an initial target position, being a virtual scene of a virtual patient in the correct position, for the detected anatomy of interest during the medical image acquisition;
    adapting a subset of the initial target position with the current spatial information of the anatomy of interest insofar said subset is clinically irrelevant for the medical image acquisition; and
    determining an adapted target position based on said adaptation.

12. Method according to claim 11, further comprising:
    generating image data of the adapted target position; and
    displaying the generated image data of the adapted target position in an overlaid manner with the anatomy of interest.

13. Method according to claim 11, further comprising:
    providing and displaying a graphical target source representation comprising augmented reality information indicating a target position of the medical imaging source for the image acquisition, and/or a graphical target detector representation comprising augmented reality information indicating a target position of the medical imaging detector for the image acquisition.

14. A non-transitory computer readable medium having one or more executable instructions stored thereon, which when executed by a processor, cause the processor to perform a method for guiding positioning of an anatomy of interest of a patient, the method comprising:
    detecting an anatomy of interest of a patient for a medical image acquisition;
    detecting current spatial information of the detected anatomy of interest;

providing an initial target position, being a virtual scene of a virtual patient in the correct position, for the detected anatomy of interest during the medial image acquisition;

adapting a subset of the initial target position with the current spatial information of the anatomy of interest insofar said subset is clinically irrelevant for the medial image acquisition; and determining an adapted target position based on said adaption.

* * * * *